(12) United States Patent
DeLuca et al.

(10) Patent No.: US 6,887,860 B2
(45) Date of Patent: May 3, 2005

(54) (20S)-1α-HYDROXY-2-METHYLENE-19-NOR-BISHOMOPREGNACALCIFEROL AND ITS USES

(75) Inventors: Hector F. DeLuca, Deerfield, WI (US); Lori A. Plum, Madison, WI (US); Margaret Clagett-Dame, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 10/462,272

(22) Filed: Jun. 16, 2003

(65) Prior Publication Data

US 2004/0033998 A1 Feb. 19, 2004

Related U.S. Application Data

(62) Division of application No. 10/078,204, filed on Feb. 18, 2002, now Pat. No. 6,627,622.

(51) Int. Cl.[7] .............................................. A61K 31/59
(52) U.S. Cl. ....................................................... 514/167
(58) Field of Search .......................................... 514/167

(56) References Cited

U.S. PATENT DOCUMENTS

| | | | |
|---|---|---|---|
| 4,666,634 A | 5/1987 | Miyamoto | |
| 4,800,198 A | 1/1989 | DeLuca et al. | |
| 5,089,641 A | 2/1992 | DeLuca et al. | |
| 5,536,713 A | 7/1996 | DeLuca et al. | |
| 5,578,587 A | 11/1996 | DeLuca et al. | |
| 5,587,497 A | 12/1996 | DeLuca et al. | |
| 5,843,928 A | 12/1998 | DeLuca et al. | |
| 5,936,133 A | 8/1999 | DeLuca et al. | |
| 5,945,410 A | 8/1999 | DeLuca et al. | |

FOREIGN PATENT DOCUMENTS

WO  WO 96/01811  1/1996

OTHER PUBLICATIONS

Brown et al, "New Active Analogues of Vitamin D with Low Calcemic Activity", Kidney International, vol. 38, Suppl. 29, 1990, pp. S–22–S–27.

Hareau et al, "Asymmetric Synthesis of 1Alpha,25–Dihydroxyvitamin D3 A–Ring Precursor Starting with 5–Tert–Butyldlmethylsiloxy–2–Cyclohexenone", Tetrahedron Letters, 41, 2000, pp. 2385–2388.

Sicinski et al, "New 1Alpha,25–Dihydroxy–19–Norvitamin D3 Compounds of High Biological Activity: Synthesis and Biological Evaluation of 2–Hydroxymethyl, 25–Methyl, and 2–Methylene Analogues", Journal of Medical Chemistry, 1998, vol. 41, No. 23, pp. 4662–4674.

Posner et al, "2–Fluoroalkyl A–Ring Analogs of 1,25–Dihydroxyvitamin D3, Stereocontrolled Total Synthesis Via Intramolecular and Intermolecular Diels–Alder Cycloadditions. Preliminary Biological Testing", Journal of Organic Chemistry, 1995, vol. 60, No. 14, pp. 4617–4628.

*Primary Examiner*—San-Ming Hui
(74) *Attorney, Agent, or Firm*—Andrus, Sceales, Starke & Sawall, LLP (57) ABSTRACT

This invention discloses (20S)-1α-hydroxy-2-methylene-19-nor-bishomopregnacalciferol and pharmaceutical uses therefor. This compound exhibits pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also has little, if any, calcemic activity and therefore may be used to treat immune disorders in humans as well as renal osteodystrophy.

6 Claims, 6 Drawing Sheets

1α, 25-DIHYDROXY-19-NORVITAMIN D3

FIG. 1A

1α,25-DIHYDROXYVITAMIN D3
A.K.A. NATIVE HORMONE

FIG. 1B

1α-HYDROXY-2-METHYLENE-
19-NOR-PREGNACALCIFEROL
A.K.A 2-Mpregna

FIG. 1C (20S)-1α-HYDROXY-2-METHYLENE-
19-NOR-BISHOMOPREGNACALCIFEROL
A.K.A 2-MbisP

FIG. 1D

1α-HYDROXY-2-METHYLENE-19-
NOR-HOMOPREGNACALCIFEROL
A.K.A 2-MP

(20S)-1α-HYDROXY-2-METHYLENE-19-NOR-BISHOMOPREGNACALCIFEROL AND ITS USES

CROSS-REFERENCE TO RELATED APPLICATIONS

This application is a divisional of application Ser. No. 10/078,204 filed Feb. 18, 2002, now U.S. Pat. No. 6,627,622.

BACKGROUND OF THE INVENTION

This invention relates to vitamin D compounds, and more particularly to (20S)-1α-hydroxy-2-methylene-19-nor-bishomopregnacalciferol and its pharmaceutical uses.

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

Recently, a new class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, an analog which is characterized by the presence of a methylene substituent at the carbon 2 (C-2) has been synthesized and tested. Of particular interest is the analog which is characterized by a hydroxyl group at carbon 1 and a shortened side chain attached to carbon 20, i.e. (20S)-1α-hydroxy-2-methylene-19-nor-bishomopregnacalciferol. This vitamin D analog seemed an interesting target because the relatively small methylene group at C-2 should not interfere with binding to the vitamin D receptor. Moreover, molecular mechanics studies performed on the model 1α-hydroxy-2-methylene-19-nor-vitamins indicate that such molecular modification does not change substantially the conformation of the cyclohexanediol ring A. However, introduction of the 2-methylene group into 19-nor-vitamin D carbon skeleton changes the character of its 1α- and 3β-A-ring hydroxyls. They are both now in the allylic positions, similarly, as 1α-hydroxyl group (crucial for biological activity) in the molecule of the natural hormone, 1α,25-$(OH)_2D_3$.

SUMMARY OF THE INVENTION

The present invention is directed toward (20S)-1α-hydroxy-2-methylene-19-nor-bishomopregnacalciferol, its biological activity, and various pharmaceutical uses for this compound.

Structurally this 19-nor analog is characterized by the general formula I shown below:

The above compound exhibits a desired, and highly advantageous, pattern of biological activity. This compound is characterized by relatively high binding to vitamin D receptors, but very low intestinal calcium transport activity, as compared to that of 1α,25-dihydroxyvitamin $D_3$, and has very low ability to mobilize calcium from bone, as compared to 1α,25-dihydroxyvitamin $D_3$. Hence, this compound can be characterized as having little, if any, calcemic activity. Thus, it may be useful as a therapy for suppression of secondary hyperparathyroidism of renal osteodystrophy.

The compound of the invention has also been discovered to be especially suited for treatment and prophylaxis of human disorders which are characterized by an imbalance in the immune system, e.g. in autoimmune diseases, including multiple sclerosis, lupis, diabetes mellitus, host versus graft reaction, and rejection of organ transplants; and additionally for the treatment of inflammatory diseases, such as rheumatoid arthritis, asthma, and inflammatory bowel diseases such as celiac disease and croans disease, as well as the improvement of bone fracture healing and improved bone grafts.

Acne, alopecia and hypertension are other conditions which may be treated with the compound of the invention.

The above compound is also characterized by relatively high cell differentiation activity. Thus, this compound also provides a therapeutic agent for the treatment of psoriasis, or as an anti-cancer agent, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

The compound may be present in a composition to treat the above-noted diseases and disorders in an amount from about 0.01 µg/gm to about 100 µg/gm of the composition, and may be administered topically, transdermally, orally or parenterally in dosages of from about 0.01 µg/day to about 100 µg/day.

DETAILED DESCRIPTION OF THE INVENTION (20S)-1α-hydroxy-2-methylene-19-nor-bishomopregnacalciferol (referred to herein as 2-MbisP) was synthesized and tested. Structurally, this 19-nor analog is characterized by the general formula I previously illustrated herein.

The preparation of (20S)-1α-hydroxy-2-methylene-19-nor-bishomopregnacalciferol having the basic structure I can be accomplished by a common general method, i.e. the condensation of a bicyclic Windaus-Grundmann type ketone II with the allylic phosphine oxide III to the corresponding 2-methylene-19-nor-vitamin D analog IV followed by deprotection at C-1 and C-3 in the latter compound:

In the structures II, III, and IV groups $Y_1$ and $Y_2$ are hydroxy-protecting groups, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure II are known, or can be prepared by known methods.

For the preparation of the required phosphine oxides of general structure III, a synthetic route has been developed starting from a methyl quinicate derivative which is easily obtained from commercial (1R,3R,4S,5R)-(—)-quinic acid as described by Perlman et al., Tetrahedron Lett. 32, 7663 (1991) and DeLuca et al., U.S. Pat. No. 5,086,191.

The overall process of the synthesis of compound I is illustrated and described more completely in U.S. Pat. No. 5,843,928 entitled "2-Alkylidene-19-Nor-Vitamin D Compounds" the specification of which is specifically incorporated herein by reference.

Figure 1A:
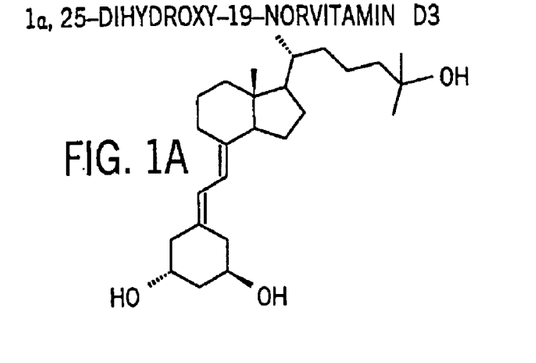
FIGS. 1A–1E illustrate the structures of the compounds described and tested herein, namely, 1α,25-dihydroxy-19-nor-vitamin $D_3$, hereinafter 1,25(OH)$_2$ 19-nor-$D_3$ (FIG. 1A); the native hormone 1α,25-dihydroxyvitamin $D_3$, hereinafter 1,25(OH)$_2D_3$ (FIG. 1B); 1α-hydroxy-2-methylene-19-nor-pregnacalciferol, hereinafter 2-Mpregna (FIG. 1C); (20S)-1α-hydroxy-2-methylene-19-nor-bishomopregnacalciferol, hereinafter 2-MbisP (FIG. 1D); and 1α-hydroxy-2-methylene-19-nor-homopregnacalciferol, hereinafter 2-MP (FIG. 1E)
Figure 1B:
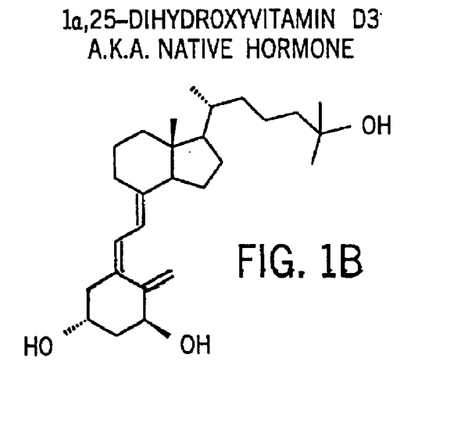
Figure 1C:
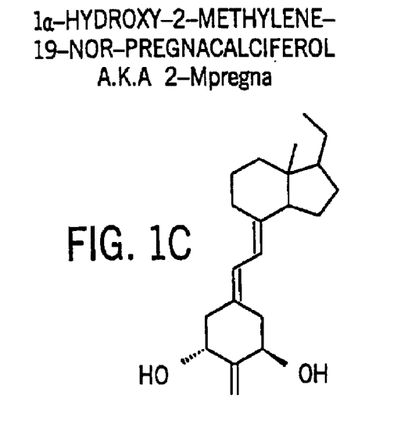
Figure 1D:
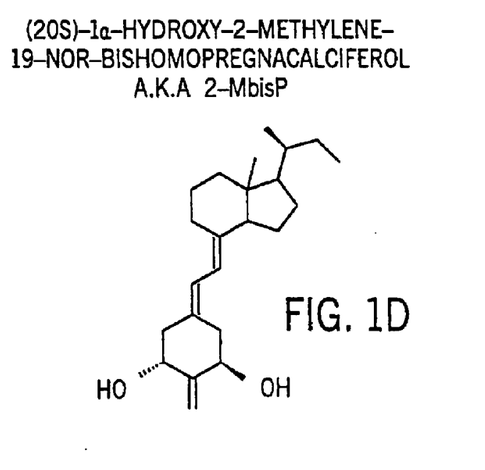
Figure 1E:
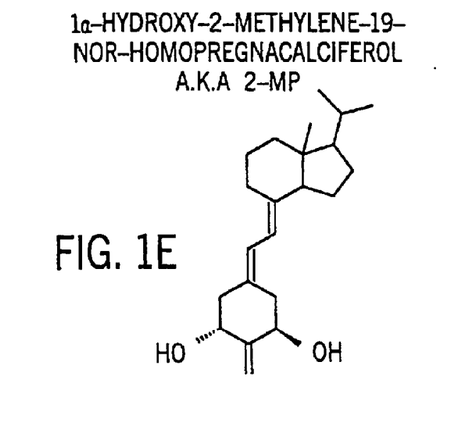
Figure 2:
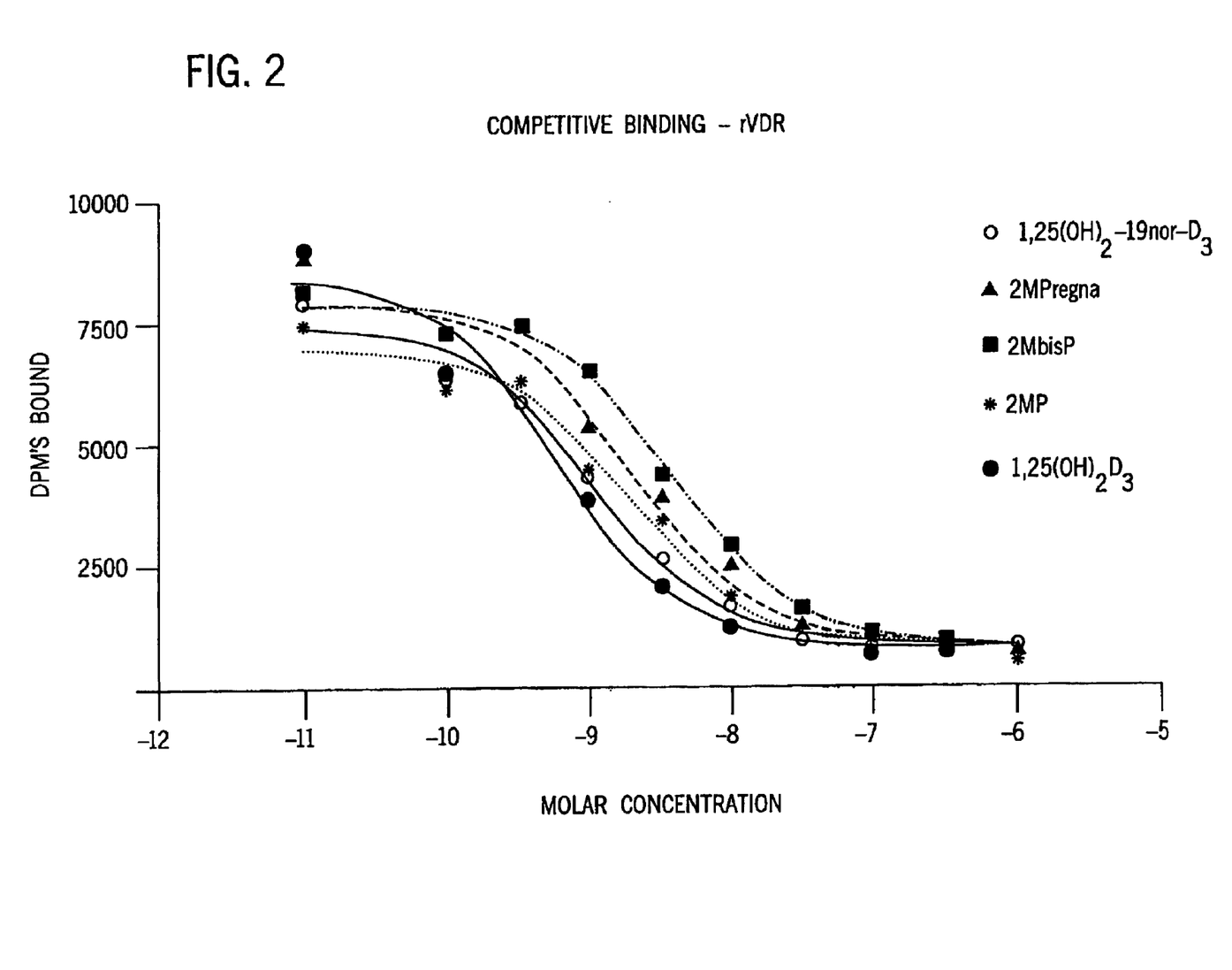
FIG. 2 is a graph illustrating the relative activity of 1,25(OH)$_2$ 19-nor-$D_3$, 2-Mpregna, 2-MbisP, 2-MP and 1,25 (OH)$_2D_3$ to compete for binding with [$^3$H]-1,25-(OH)$_2$-$D_3$ to the full-length recombinant rat vitamin D receptor.

Biological Activity of (20S)-1α-Hydroxy-2-Methylene-19-Nor-Bishomopregnacalciferol The introduction of a methylene group to the 2-position of 1α-hydroxy-19-nor-pregnacalciferol had little or no effect on binding to the porcine intestinal vitamin D receptor, as compared to 1α,25-dihydroxyvitamin $D_3$. This compound bound equally well to the porcine receptor as compared to the standard 1,25-$(OH)_2D_3$ (FIG. 2). It might be expected from these results that this compound would have equivalent biological activity. Surprisingly, however, the 2-methylene substitution in 2-MbisP produced a highly selective analog with unique biological activity.

Figure 4A:
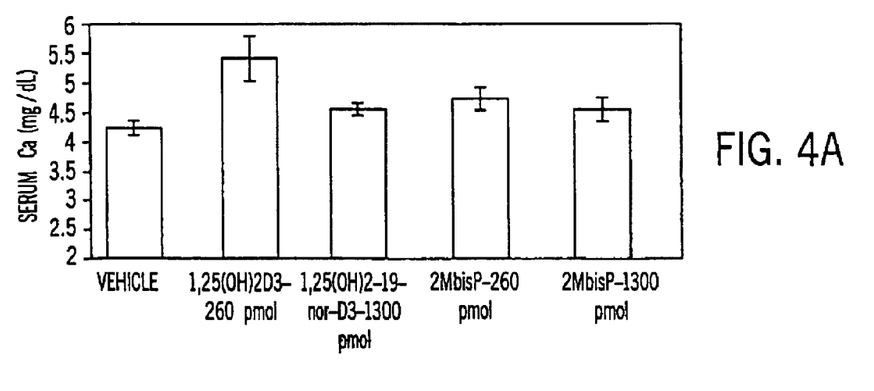
FIGS. 4A–4C are bar graphs illustrating the bone calcium mobilization activity of 1,25(OH)$_2D_3$ and 1,25(OH)$_2$ 19-nor-$D_3$ as compared to 2-MbisP (FIG. 4A), 2-Mpregna (FIG. 4B), and 2-MP (FIG. 4C)
Figure 4B:
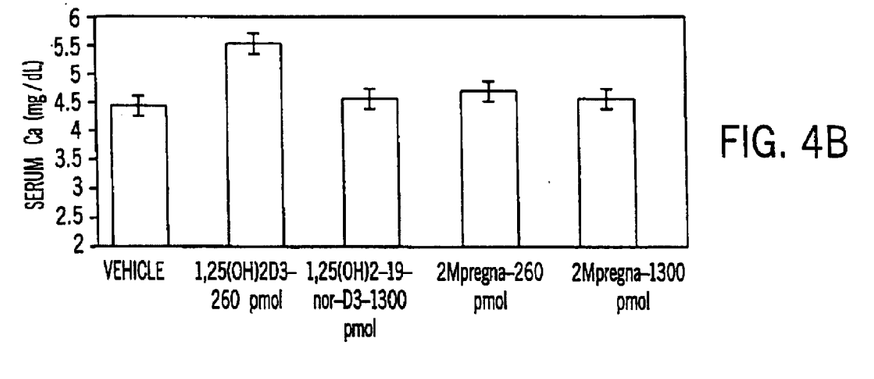

FIG. 4B shows that 2-MbisP has very little activity as compared to that of 1,25-dihydroxyvitamin $D_3$ (1,25$(OH)_2D_3$), the natural hormone, in stimulating intestinal calcium transport.

Figure 5A:
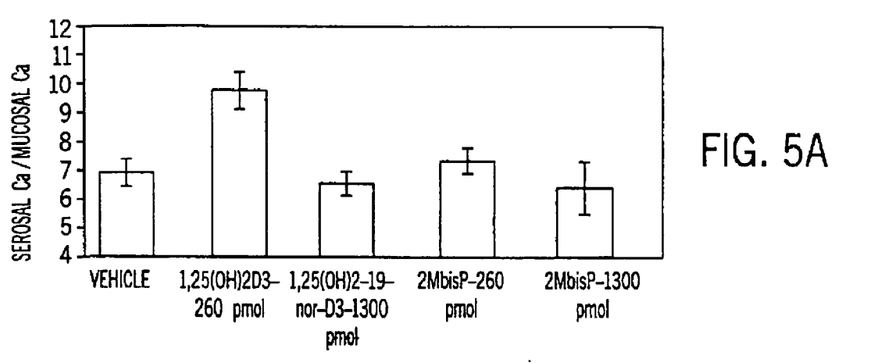
FIGS. 5A–5C are bar graphs illustrating the intestinal calcium transport activity of 1,25(OH)$_2D_3$ and 1,25(OH)$_2$ 19-nor-$D_3$ as compared to 2-MbisP (FIG. 4A), 2-Mpregna (FIG. 4B), and 2-MP (FIG. 4C)
Figure 5B:
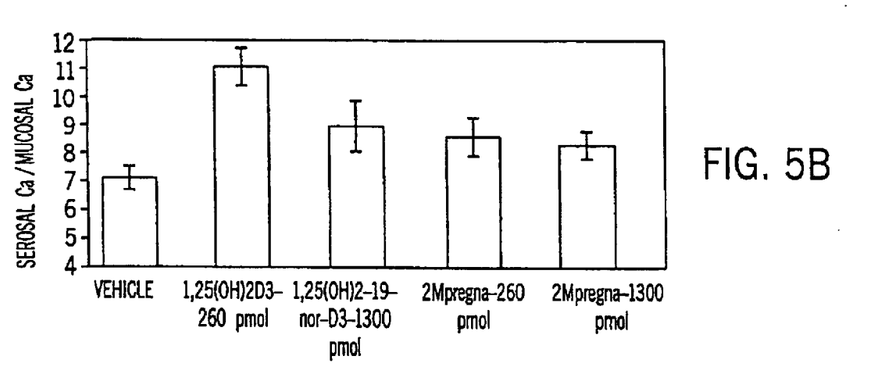

FIG. 5B demonstrates that 2-MbisP has very little bone calcium mobilization activity, as compared to 1,25$(OH)_2D_3$.

FIGS. 4B and 5B thus illustrate that 2-MbisP may be characterized as having little, if any, calcemic activity.

Figure 3:
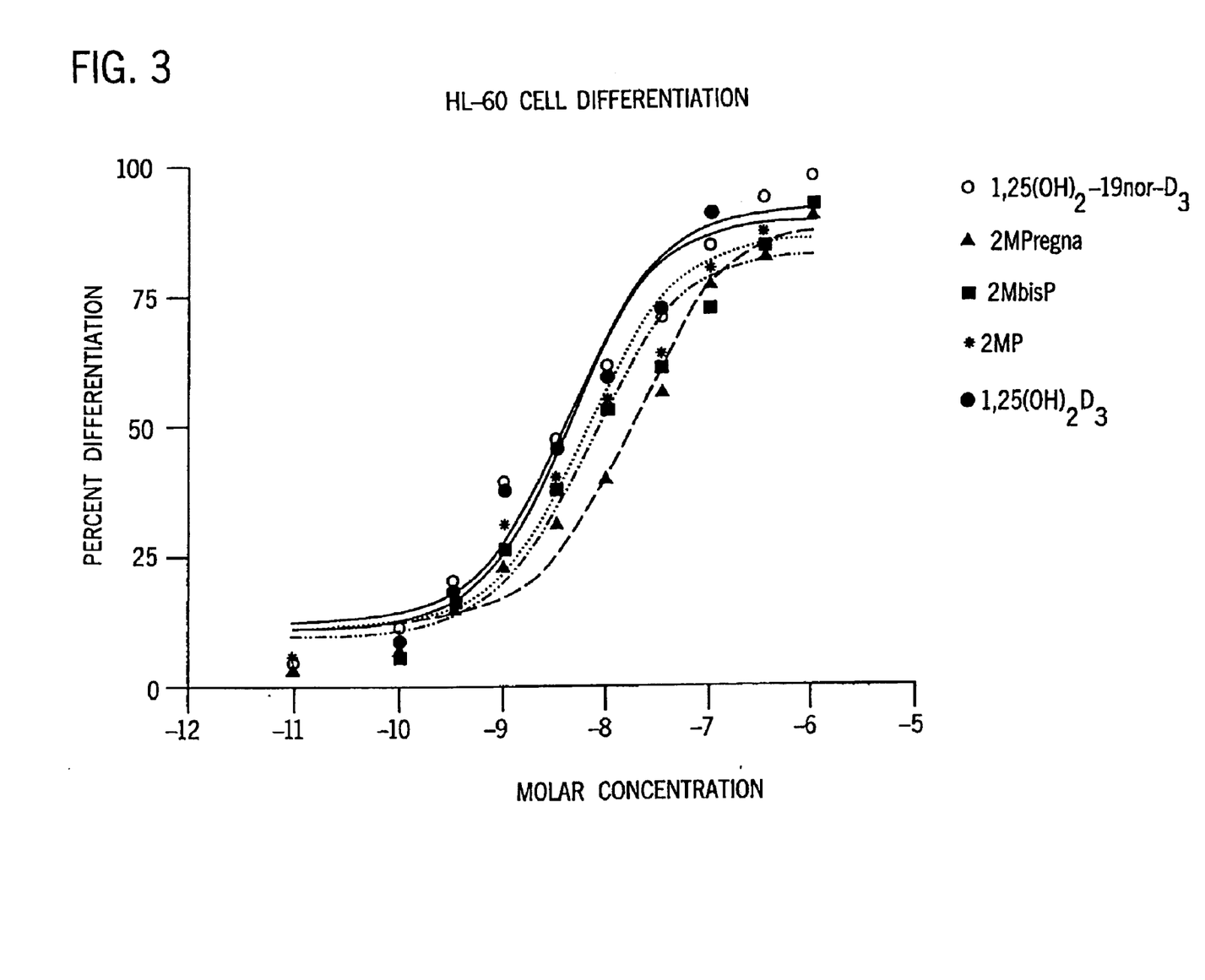
FIG. 3 is a graph illustrating the percent HL-60 cell differentiation as a function of the concentration of 1,25 (OH)$_2$ 19-nor-$D_3$, 2-Mpregna, 2-MbisP, 2-MP and 1,25(OH)$_2D_3$.

FIG. 3 illustrates that 2-MbisP is almost as potent as 1,25$(OH)_2D_3$ on HL-60 differentiation, making it an excellent candidate for the treatment of psoriasis and cancer, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 6:
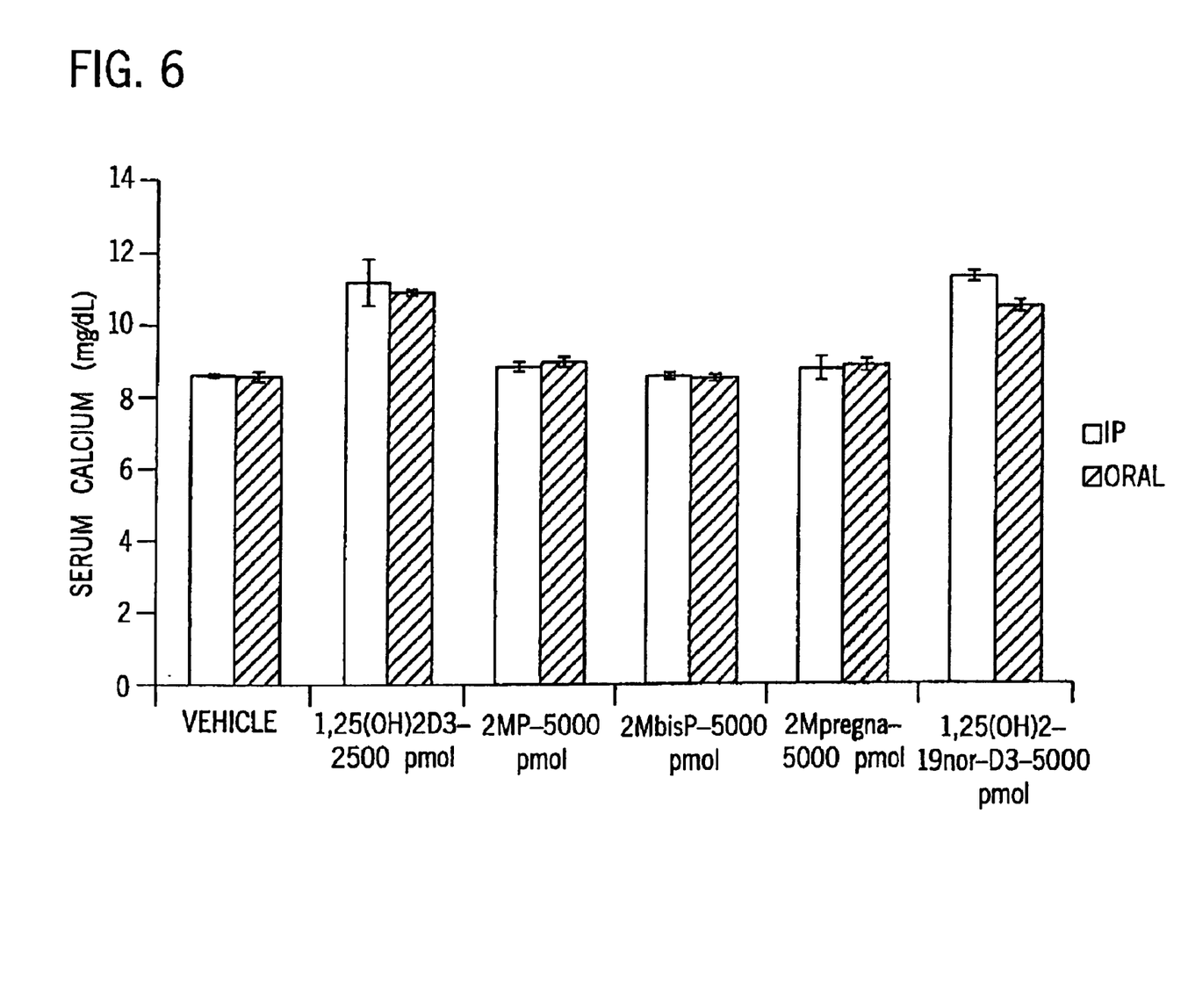
FIG. 6 is a bar graph illustrating blood serum calcium levels in female rats after treatment with chronic doses of 1,25(OH)$_2D_3$ and 1,25(OH)$_2$ 19-nor-$D_3$ as compared to 2-MbisP, 2-Mpregna, and 2-MP.

FIG. 6 shows an analysis of serum calcium in rats after administration of chronic doses of 2-MbisP. These data provide further support for the data in FIGS. 4B and 5B that 2-MbisP has very little calcemic activity and thus a relatively low risk of producing hypercalcemia at recommended doses.

The battery of in vitro and in vivo assays described in Sicinski et al (J. Med. Chem. 41, 4662–4674, 1998) were used to compare the biological activities of the compounds, 2-Mpregna, 2-MbisP and 2-MP, with 1,25$(OH)_2$ 19-nor-$D_3$, and 1,25$(OH)_2D_3$, the native vitamin D hormone.

The differentiation of HL-60 promyelocytic into monocytes was determined as described by Ostrem et al (J. Biol. Chem. 262, 14164–14171, 1987).

Interpretation of Data

VDR binding and HL60 cell differentiation. 2-MbisP, 2-Mpregna and 2-MP are nearly equivalent (Ki=0.3, 0.6 and 0.3 nM for 2-Mpregna, 2-MbisP and 2-MP, respectively) in their ability to compete with [$^3$H]-1,25$(OH)_2D_3$ for binding to the full-length recombinant rat vitamin D receptor (FIG. 2). Furthermore, the competition binding activity of these three compounds is similar to that of 1,25$(OH)_2$ 19-nor-$D_3$ (Ki=0.2 nM), as well as the native hormone, 1,25$(OH)_2D_3$ (Ki=0.1 nM). There is little difference between any of these five compounds in their ability (efficacy or potency) to promote HL60 differentiation with the possible exception of 2-Mpregna ($EC_{50}$=17 nM), which is slightly less potent than 2-MbisP ($EC_{50}$=7 nM), 2-MP ($EC_{50}$=6 nM), 1,25$(OH)_2$ 19-nor-$D_3$ ($EC_{50}$=4 nM) and 1,25$(OH)_2D_3$ ($EC_{50}$=5 nM) (See FIG. 3). This result suggests that 2-MbisP will be very effective in psoriasis because it has direct cellular activity in causing cell differentiation and in suppressing cell growth. It also indicates that it will have significant activity as an anti-cancer agent, especially against leukemia, colon cancer, breast cancer and prostate cancer, as well as against skin conditions such as dry skin (lack of dermal hydration), undue skin slackness (insufficient skin firmness), insufficient sebum secretion and wrinkles.

Figure 4C:
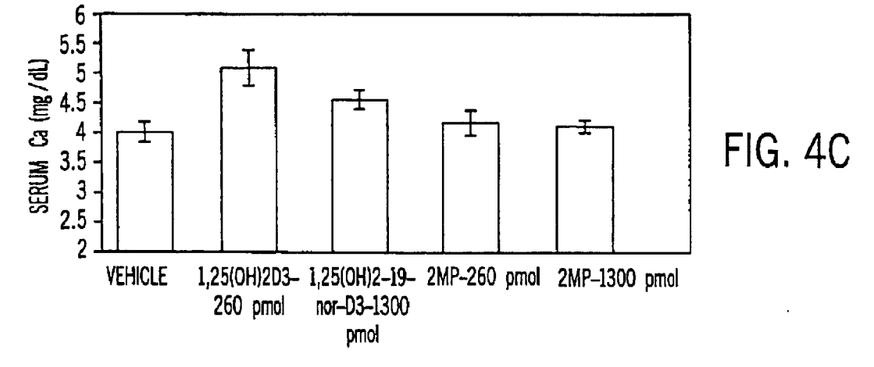

Calcium mobilization from bone and intestinal calcium absorption in vitamin D-deficient animals. Using vitamin D-deficient rats on a low calcium diet (0.02%), the activities of these compounds in intestine and bone were tested. As expected, the native hormone (1,25$(OH)_2D_3$) increased serum calcium levels at all dosages (FIG. 4). FIG. 4 also shows that 2-MbisP, 2-Mpregna and 2-MP have little, if any, activity in mobilizing calcium from bone. Administration of 2-MbisP, 2-Mpregna, 2-MP or 1,25$(OH)_2$ 19-nor-$D_3$ at 260 pmol/day for 7 days did not result in mobilization of bone calcium, and increasing the amount of 2-MbisP, 2-Mpregna and 2-MP to 1300 pmol/day (5-fold) was without effect. Similar findings were obtained with 1,25$(OH)_2$ 19-nor-$D_3$.

Figure 5C:
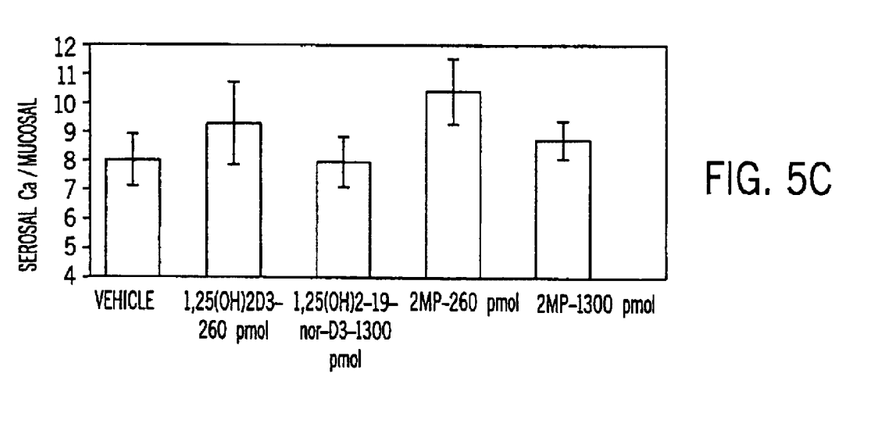

Intestinal calcium transport was evaluated in the same groups of animals using the everted gut sac method (FIG. 5). These results show that 2-MbisP and 2-Mpregna do not promote intestinal calcium transport when administered at either 260 or 1300 pmol/day, whereas 1,25$(OH)_2D_3$ promotes a significant increase at the 260 pmol/day dose. In contrast to 2-MbisP and 2-Mpregna, 2-MP showed calcium transport activity equivalent to 1,25$(OH)_2D_3$ at this and the 5-fold higher concentration but higher doses actually decreased this activity. As shown in FIG. 4, 1,25$(OH)_2$ 19-nor-$D_3$, like the 2-MbisP and 2-Mpregna derivatives, is devoid of intestinal calcium transport activity.

Serum calcium response in vitamin D-sufficient animals on a normal calcium diet. The desirability of 2-MbisP, 2-Mpregna and 2-MP is exemplified by their inability to produce hypercalcemia in normal animals compared to 1,25$(OH)_2$ 19-nor-$D_3$, and 1,25$(OH)_2D_3$. In the experiment shown in FIG. 6, normal, female rats were given 2500 pmol/day for 7 days of 1,25$(OH)_2D_3$, or 5000 pmol/day of 2-MbisP, 2-Mpregna, 2-MP or 1,25$(OH)_2$ 19-nor-$D_3$. The doses were administered to two separate groups of animals by either the oral or intraperitoneal route, and serum calcium levels were assessed 4 hours after the last dose. Animals receiving 1,25$(OH)_2D_3$ by either route exhibited hypercalcemia, some severe enough to require euthanasia. Likewise, 1,25$(OH)_2$ 19-nor-$D_3$ produced frank hypercalcemia. In contrast, no increase in serum calcium was seen in any of the animals receiving the compounds, 2-MP, 2-MbisP or 2-Mpregna.

These results illustrate that 2-MbisP is an excellent candidate for numerous human therapies and that it may be useful in a number of circumstances such as autoimmune diseases, cancer, and psoriasis. 2-MbisP is an excellent candidate for treating psoriasis because: (1) it has significant VDR binding and cellular differentiation activity; (2) it is devoid of hypercalcemic liability unlike 1,25$(OH)_2$ 19-nor-$D_3$ and 1,25$(OH)_2D_3$; and (3) it is easily synthesized. Since 2-MbisP has significant binding activity to the vitamin D receptor, but has little ability to raise blood serum calcium, it may also be useful for the treatment of renal osteodystrophy.

For treatment purposes, the compound of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compound may be administered orally, topically, parenterally or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.01 μg to 100 μg per day of the compounds are appropriate for treatment purposes, such doses being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the (20S)-1α-hydroxy-2-methylene-19-nor-bishomopregnacalciferol as defined by the above formula I as the active ingredient, and a suitable carrier. An effective amount of such compound for use in accordance with this invention is from about 0.01 μg to about 100 μg per gm of composition, and may be administered topically, transdermally, orally or parenterally in dosages of from about 0.01 μg/day to about 100 μg/day.

The compound may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compound is advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A method of treating psoriasis comprising administering to a patient with psoriasis an effective amount of (20S)-1α-hydroxy-2-methylene-19-nor-bishomopregnacalciferol having the formula:

2. The method of claim 1 wherein (20S)-1α-hydroxy-2-methylene-19-nor-bishomopregnacalciferol is administered orally.

3. The method of claim 1 wherein (20S)-1α-hydroxy-2-methylene-19-nor-bishomopregnacalciferol is administered parenterally.

4. The method of claim 1 wherein (20S)-1α-hydroxy-2-methylene-19-nor-bishomopregnacalciferol is administered transdermally.

5. The method of claim 1 wherein (20S)-1α-hydroxy-2-methylene-19-nor-bishomopregnacalciferol is administered topically.

6. The method of claim 1 wherein (20S)-1α-hydroxy-2-methylene-19-nor-bishomopregnacalciferol is administered in a dosage of from about 0.01 μg/day to about 100 μg/day.

* * * * *